(12) United States Patent
Berger

(10) Patent No.: US 7,583,865 B2
(45) Date of Patent: Sep. 1, 2009

(54) SEGMENTED FIBER OPTIC SENSOR AND METHOD

(75) Inventor: Alexander Berger, Torrance, CA (US)

(73) Assignee: Optech Ventures, LLC, Torrance, CA (US)

( * ) Notice: Subject to any disclaimer, the term of this patent is extended or adjusted under 35 U.S.C. 154(b) by 27 days.

(21) Appl. No.: 11/233,332

(22) Filed: Sep. 22, 2005

(65) Prior Publication Data

US 2007/0065070 A1      Mar. 22, 2007

(51) Int. Cl.
G02B 6/00 (2006.01)
(52) U.S. Cl. .................................................. 385/12
(58) Field of Classification Search .................. 385/12
See application file for complete search history.

(56) References Cited

U.S. PATENT DOCUMENTS

| | | | |
|---|---|---|---|
| 4,399,099 A | 8/1983 | Buckles | |
| 4,474,426 A | 10/1984 | Yataki | |
| 4,706,677 A * | 11/1987 | Goorsky et al. | 600/342 |
| 4,758,298 A * | 7/1988 | Goorsky et al. | 156/296 |
| 4,834,496 A | 5/1989 | Blyler, Jr. et al. | |
| 4,865,416 A * | 9/1989 | Pratt | 385/12 |
| 4,907,857 A | 3/1990 | Giuliani et al. | |
| 5,047,627 A | 9/1991 | Yim et al. | |
| 5,335,305 A | 8/1994 | Kosa et al. | |
| 6,205,263 B1 | 3/2001 | Lieberman et al. | |
| 6,328,932 B1 * | 12/2001 | Carter et al. | 422/82.06 |
| 6,449,400 B1 | 9/2002 | Watanabe et al. | |
| 6,694,067 B1 | 2/2004 | O'Keefe et al. | |
| 7,123,801 B2 | 10/2006 | Fitz | |
| 7,209,605 B2 * | 4/2007 | Cantin et al. | 385/12 |
| 2005/0168749 A1 | 8/2005 | Ye et al. | |
| 2005/0213867 A1 * | 9/2005 | Rajendran et al. | 385/12 |

OTHER PUBLICATIONS

KTV Grattan and BT Meggitt, Optical Fiber Sensor Technology, 2002, pp. 241-244, Kluwer Academic Publishers.
Francis TS Yu and Shizhuo Yin, Fiber Optic Sensors, 2002, pp. 183-188, CRC Press.

* cited by examiner

*Primary Examiner*—Sung H Pak
(74) *Attorney, Agent, or Firm*—Lawrence S. Cohen

(57) ABSTRACT

A fiber optic sensor for sensing the presence of an analyte has a plurality of optical fibers each of which has an analyte sensing segment and the fibers are deployed so that the analyte sensing segments are arranged in sequential offset relationship over a distance such that each segment is available for detecting the analyte over a part of the distance. This has the advantage that detection of an analyte can be spatially resolved to the location of the one or more segments that have responded to the presence of the analyte. It also has the advantage that the high attenuation of sensing segments is reduced due to the smaller distance traversed by each sensing segment. Also multiple sets of such fibers may be deployed in order to detect multiple analytes, each set being constructed for a particular analyte. Also a fiber carrying structure is shown that allows the sensing segments to be available for detection of analytes and to conduct lead portions of the fibers to and from the sensing segments. A system also employs light energy sources and detectors and a processor for determining response of a sensing segment to an analyte exposure.

56 Claims, 11 Drawing Sheets

US 7,583,865 B2

SEGMENTED FIBER OPTIC SENSOR AND METHOD

FIELD

This invention relates to optical sensors and more particularly to fiber optic sensors, which are configured to detect the presence of one or more analytes.

BACKGROUND

Optical fibers including materials which react in the presence of an analyte to alter the characteristics of light transmitted in the fiber are well known. U.S. Pat. No. 4,399,099 issued Aug. 11, 1983, for example, discloses fiber optic sensors for chemical and biochemical analysis, which employ an energy transmissive core with one or more coatings. The sensors are operative to modify energy passing through the core when an analyte is present. U.S. Pat. No. 4,834,496, issued May 30, 1989 also describes fiber optic sensors operating in a similar manner.

U.S. Pat. No. 6,205,263 issued May 20, 2001 describes a fiber optic sensor configured to exhibit uniform power loss along the length of the fiber optic sensors in order to achieve a predictable, preferably uniform, response to the presence of an analyte anywhere along the fiber length.

Fiber optic sensors designed to be operative over a long distance suffer increasing losses as a function of length. The high optical attenuation results in increasing difficulty in obtaining a usable signal indicative of the presence of an analyte. Therefore, there is a need in the art for fiber optic sensors that can provide signal levels at higher levels over longer distances. Also, if sensor surveillance is needed over a long continuous distance or at separated intervals over a long distance, it is desirable to be able to determine the location at which a sensing event has occurred.

SUMMARY

This summary is intended as an introductory statement and should not be taken as a recitation or an exact statement of all inventive aspects or of the content of each claim.

Embodiments of the present invention have one or more fiber optic sensing segments which are connected or spliced into or formed integrally with low attenuation lead portions to achieve practical signal levels. See the special definition of "optical fiber" and "fiber" as used herein.

In accordance with an embodiment of the present invention, a fiber optic sensor for the detection of an analyte comprises a plurality of optical fibers. Each optical fiber has a sensing segment which has a length that is a fraction of the total length of the optical fiber and the sensing segments are located in offset (see the special definition of this term) positions over the length of the sensor. The sensing segments are then deployed at positions where the detection of analyte is desired.

In one aspect the sensing segments are deployed to provide continuous detection of one analyte over a desired distance. For example, four sensing segments, each of length L/4, may be disposed in contiguous (see the special definition of this term) positions to detect the presence of an analyte over the entire length L. Each of such segments is a fractional portion of an optical fiber of length L where the remaining 3L/4 length of the optical fiber, consisting of lead portions (see the special definition of this term) in each instance, has low attenuation compared to the attenuation of the analyte-sensing segment. The resulting bundle of (4) fibers is bundled and connected to a light source and a detector.

In a more general aspect of the invention the sensing segments may be of differing length or of the same length. For example the length of the sensing segments may be selected to accommodate the installation conditions.

In another broad aspect, the sensing segments for a given analyte are offset (see the special definition of this term). Such offset configuration therefore includes overlapping, contiguous and spaced apart. Where apparatus is configured for more than one analyte the sensing segments for different analytes need not be offset.

The sensing segments may also be deployed to provide detection of an analyte at selected and non-contiguous intervals over a desired distance, that is, they may be spaced apart. The sensing segments may have the same or different lengths or some of each.

The optical fibers may be supported by an elongated spine and protected by a cable sheath having openings such as a braid to allow an analyte to reach the fibers.

Light can be launched into one end of the fibers and received at the other end in transmission mode or the light may be launched and received at the same end of the fibers in reflection mode if a reflection element is disposed at the opposite end of the fibers.

DETAILED DESCRIPTION

Figure 1:
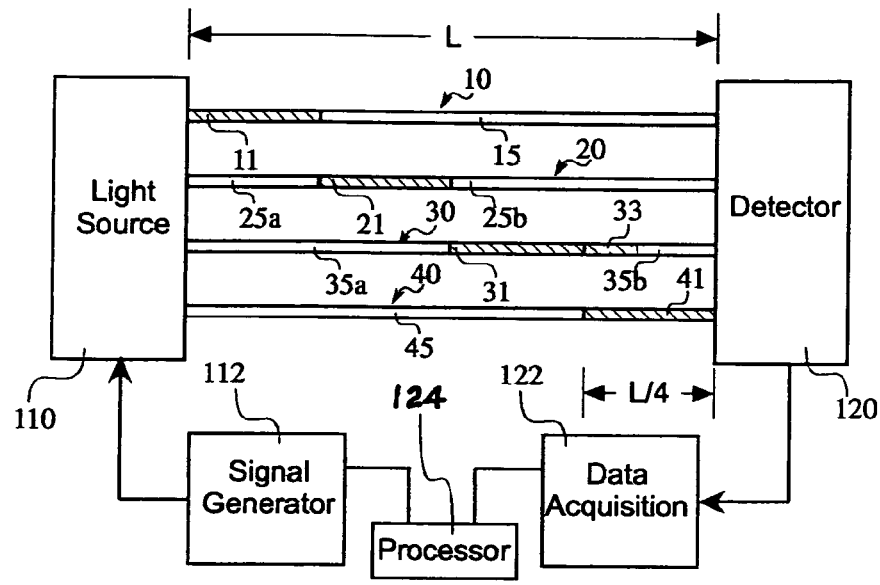
FIG. 1 is a schematic diagram of an illustrative embodiment of a segmented sensor according to the invention.

As used herein the following terms have the following meaning unless the context requires otherwise:

"optical fiber" and "fiber" refers to a functional length of one or more optical fibers that allows transmission of an optical signal from one end to another end or to a reflection element and back, as such it may be a continuous integral length of optical fiber and it may also be a series of connected or spliced lengths of optical fiber. An optical fiber determined by connectors or splicing is made up of portions of the optical fiber.

"segment", "sensing segment", "sensor segment", "analyte-responsive segment" and "analyte-sensing segment" refer to a length of optical fiber that is rendered able to react to the presence of an analyte so as to alter an optical signal sent through the optical fiber. This term, when so indicated by the context can also refer to a sensing segment that responds to environmental conditions such temperature and humidity.

"lead portions" and "non-analyte sensing portions" means a length of optical fiber not treated to react to an analyte or to have any sensing chemistry.

"offset" with reference to the relative lengthwise relationship of sensing segments in different optical fibers means any such relationship that allows substantially continuous sensing surveillance over a distance, as such it includes any one or combination of sensing segments that are contiguous or overlapping, each of which is also defined herein.

"contiguous" with reference to the lengthwise relationship of sensing segments in different optical fibers means that one ends where another begins so as to provide substantial (not necessarily exact-see further) continuity of surveillance over a distance. Accordingly, the term contiguous is also intended to include the configuration where only a connector or fusion splice or other instrumentality creates a linear space between the end of one sensing segment on one fiber and the beginning of another sensing segment on another fiber such that the distance being surveilled is substantially continuous even though there is a nominal space caused by the connector or splice or other instrumentality thereby being effective for detection of an analyte that is relatively spatially spread in the local area. This is distinguished from spaced-apart segments where the place or distance being surveilled by different sensing segments is intended to be distinguishable and substantially separated as defined below.

"overlapping" with reference to the lengthwise relationship of sensing segments means that a portion of one occupies a distance that is also occupied by a portion of another but that each occupies a distance not occupied by the other.

"spaced apart" with reference to the lengthwise relationship of sensing segments means that there is a substantial distance between the end of one and the beginning of another so that each segment has surveillance of a discrete location;

"chemical" and "analyte" are synonymous when used to describe or to define material that can be sensed by a sensing segment and are not limited to any type of chemical.

Figure 4A:
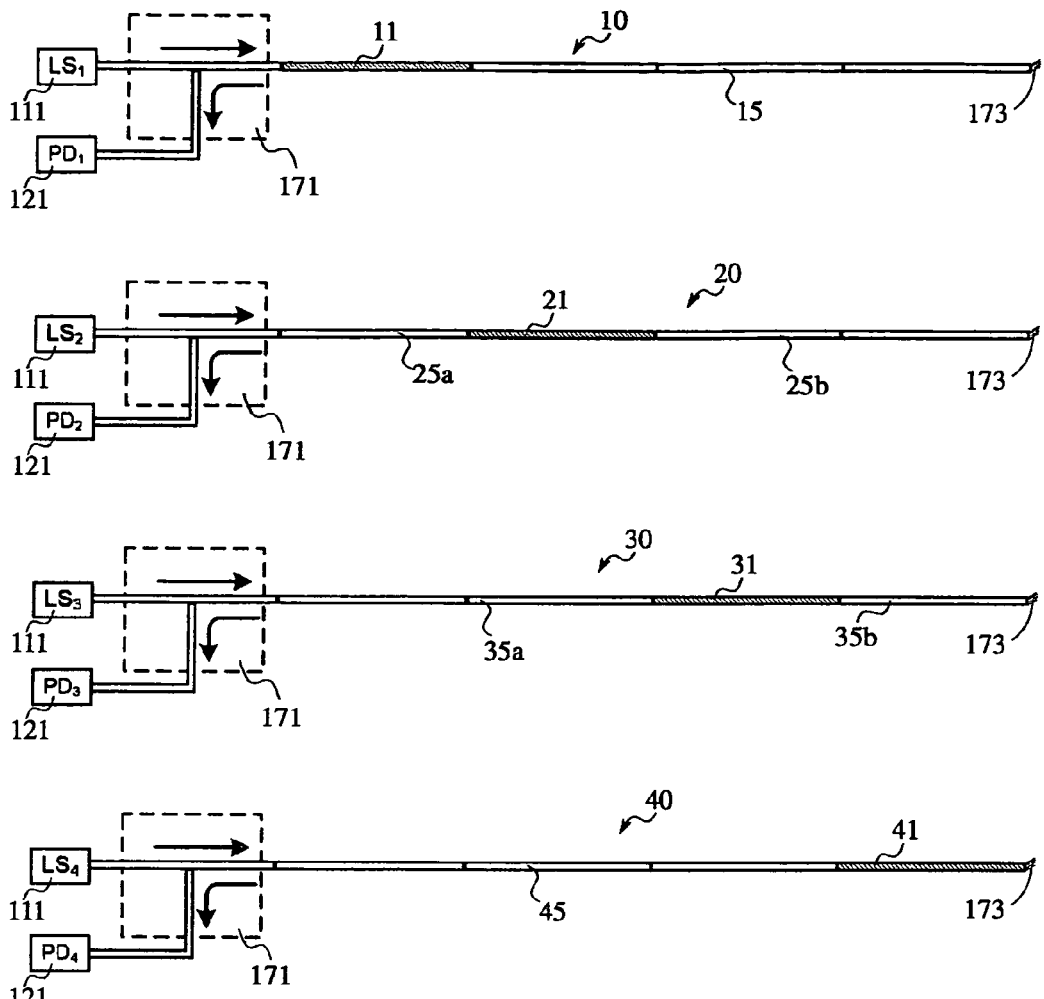
FIG. 4A shows an embodiment of the present invention where reflection elements are used to reflect light from light sources back to light detectors located at the same end of the fibers.
Figure 4B:
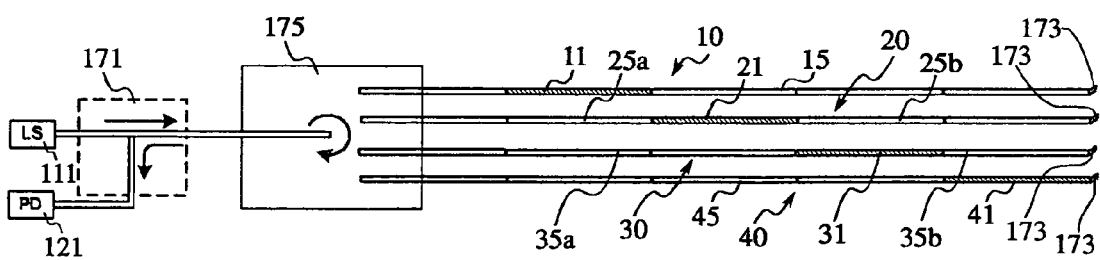
FIG. 4B shows an embodiment of the present invention where a single light source is used to transmit light into fibers having reflection elements and the light is reflected back to a single detector located at the same end of the fibers as the light source.

FIG. 1 is a schematic representation of a segmented sensor in accordance with an embodiment of this invention. The sensor is designed to sense the presence of an analyte anywhere over an arbitrary distance L. In accordance with the invention, a plurality of sensor segments are arranged in offset positions such that N sensors, each of length L/N occupy the entire distance L, however, as will be further explained the sensor segments do not have to be of equal length. In the illustrative embodiment of FIG. 1, there are four fibers 10, 20, 30, 40 (i.e., N=4) and each fiber has an analyte-sensing segment 11, 21, 31, 41. Each fiber 10, 20, 30, 40 also has one or more lead portions 15, 25a, 25b, 35a, 35b, 45. Preferably (for this embodiment), the sensing segments 11, 21, 31, 41 are of equal length (L/4). The remainder (3L/4) (indicated by lead portions 15, 25a, 25b, 35a, 35b, 45 in FIG. 1) of each fiber 10, 20, 30, 40 is preferably optimized for light transmission. The high attenuation analyte-sensing segments 11, 21, 31, 41 having lengths of L/4 may be spliced or otherwise coupled with the one or more lead portions 15, 25a, 25b, 35a, 35b, 45 comprising low attenuation lead portions having total lengths of 3L/4 to provide the desired sensing length L. In the embodiment of the present invention depicted in FIG. 1, the analyte-sensing segments 11, 21, 31, 41 are shown as equal length and additive, that is contiguous, to extend to length L. However, alternative embodiments of the present invention may have analyte-sensing segments 11, 21, 31, 41 with unequal lengths. Other embodiments of the present invention may have analyte-sensing segments 11, 21, 31, 41 that overlap one or more other sensing segments of other fibers 10, 20, 30, 40. Such an overlap is indicated by the segment 33 in FIG. 1. As discussed below, still other embodiments of the present invention may have equal length or unequal length analyte-sensing segments spaced apart from one another. As also shown in FIG. 1, the fibers 10, 20, 30, 40 are connected between a light source 110 under the control of a signal generator 112 and a detector 120 operative to transmit to a data acquisition system 122. A processor module 124 determines from the detected signal whether there is indication that an analyte has reacted with the detection chemistry of any of the sensor segments. A common type of response is calorimetric. This is preferably done by comparing the received optical energy that has passed through the sensor segments with the source optical energy. It is also possible to measure the received optical energy with a previously established baseline to determine change. Those skilled in the art will recognize that other devices or means may also be used to provide optical energy to the fibers 10, 20, 30, 40 and/or receive optical energy from the fibers 10, 20, 30, 40. It should be understood that the sensor system can be operated in reflection mode as well as in transmission mode that is illustrated and described. That is, optical energy may be transmitted and received at the same end of an optical fiber due to the reflection of the optical energy as it propagates within the fiber. FIGS. 4A and 4B show embodiments of the present invention using optical energy reflection.

Figure 2A:
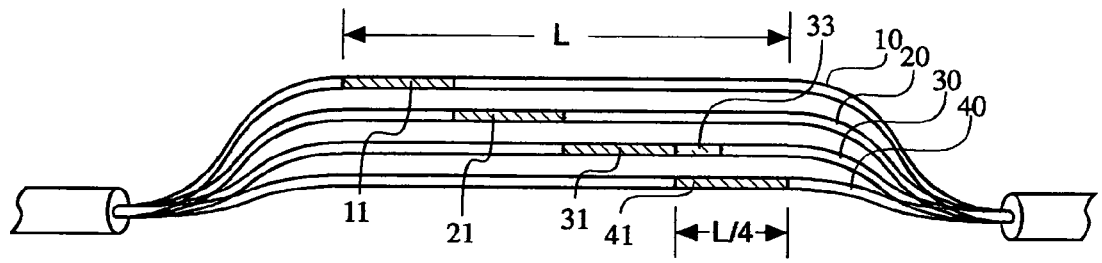
FIG. 2A is a schematic diagram of an embodiment of the present invention in which sensing segments are contiguous and/or overlapping.
Figure 2B:
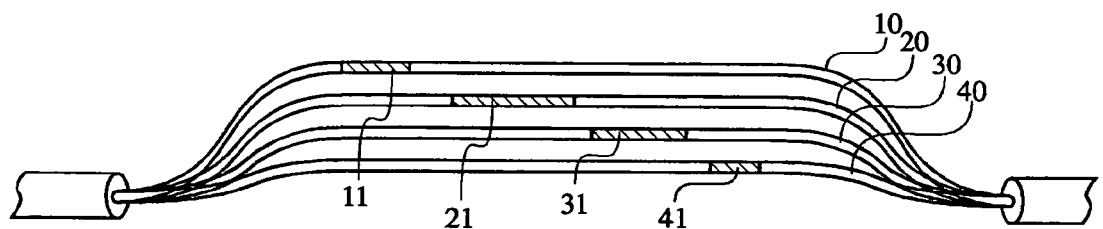
FIG. 2B is a schematic diagram of an embodiment of the present invention where sensing segments are not contiguous.

FIG. 2A illustrates the fibers of FIG. 1 in a bundled configuration, at least at the ends thereof being adapted for ease of connection to the light source 110 and detector 120. FIG. 2A also shows that the analyte-sensing segments 11, 21, 31, 41 are disposed in a contiguous manner. Also, an overlap is illustrated at 33. Consequently, analyte-sensing segments 11, 21, 31, 41 are present at each point along the entire distance L of the bundled configuration, which provides the ability to detect analyte presence anywhere along the bundle and to spatially resolve it to the portion of the distance L occupied by the sensing segment or segments that have been exposed to the analyte. FIG. 2B shows an embodiment of the present invention in which the analyte sensing segments 11, 21, 31, 41 are non-contiguous such that there are gaps between the analyte sensing segments 11, 21, 31, 41 from fiber to fiber. In the configuration depicted in FIG. 2B, analyte presence can be located at the discrete spaced-apart areas in which each of the sensing segments 11, 21, 31, 41 are deployed.

Alternative embodiments of the present invention may use different apparatus to implement the light source 110 and the detector 120 shown in FIG. 1. FIGS. 3A-3F depict some of the alternatives that may be used to provide the light source 110 and/or the detector 120. FIGS. 3A-3F show an exemplary four fiber embodiment of the present invention, but those skilled in the art will understand that other embodiments may have less than four fibers or more than four fibers and also that the sensing segments may be offset, including contiguous or overlapping or they may be spaced-apart or any combination thereof as described above. In FIGS. 3A-3F, each optical fiber 10, 20, 30, 40 has a sensing segment 11, 21, 31, 41 and one or more lead portions 15, 25A, 25b, 35a, 35b, 45.

Figure 3A:
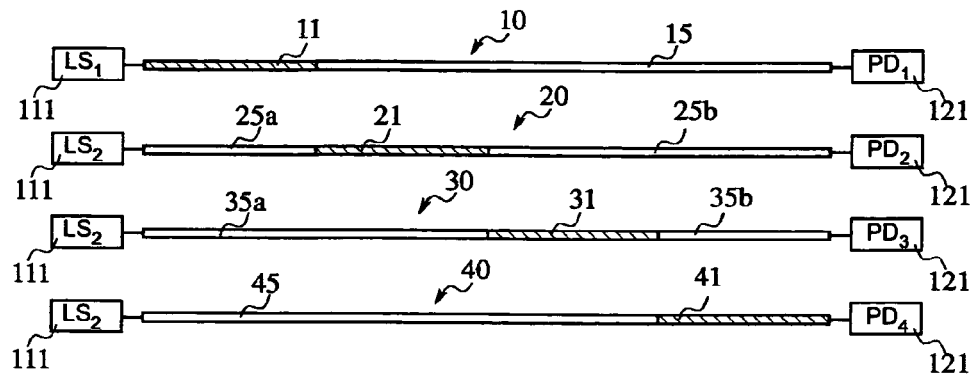
FIGS. 3A-3F depict alternative optical energy sources and optical energy detectors according to embodiments of the present invention.

FIG. 3A shows an embodiment of the present invention in which each fiber 10, 20, 30, 40 is illuminated by a dedicated light source 111 and the optical output is measured by a dedicated photodetector 121. As can be seen from FIG. 3A, N optical fibers will then require N light sources and N photodetectors.

Figure 3B:
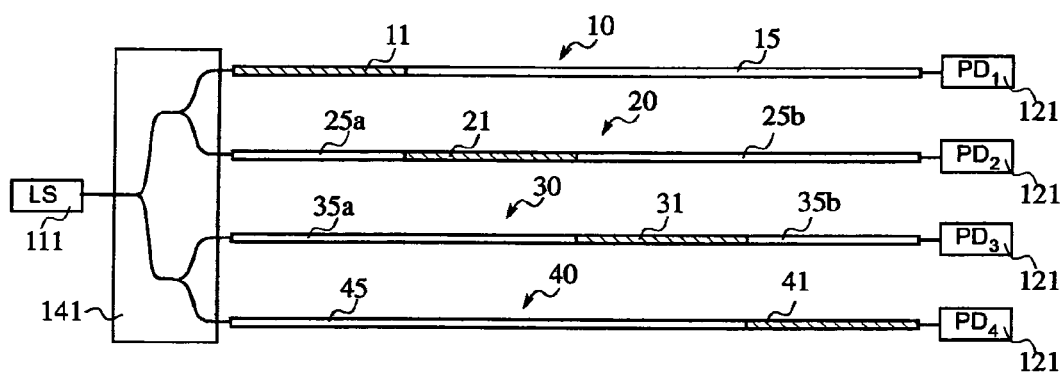

FIG. 3B shows an embodiment of the present invention in which a series of optical splitters 141 couples light from a single light source 111 into N optical fibers 10, 20, 30, 40. The optical outputs from the N optical fibers 10, 20, 30, 40 are measured by N dedicated photodetectors 121. An alternative embodiment may use an optical switch (not shown) in place of the optical splitter.

Figure 3C:
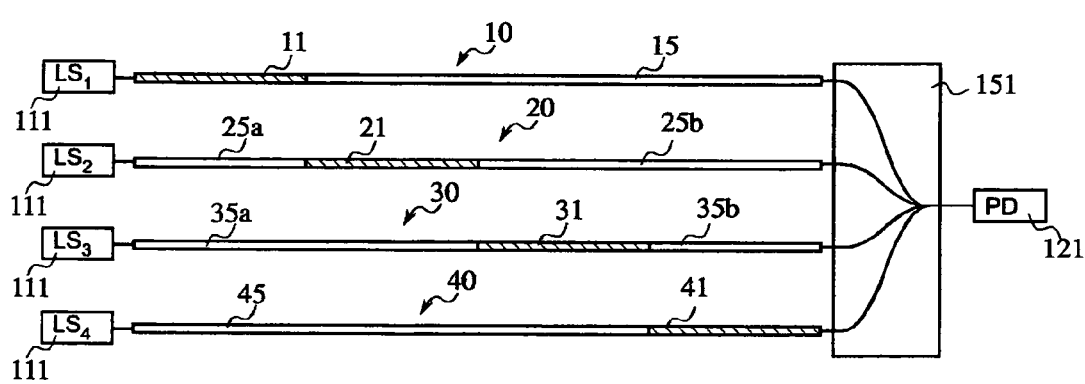

FIG. 3C shows an embodiment of the present invention in which N light sources 111 provide light to N optical fibers 10, 20, 30, 40. The outputs from the N optical fibers are combined using an N×1 optical coupler 151, which directs the combined optical signal to a single photodetector 121. Preferably, the optical signals from the light sources are separated using Time Division Multiplexing (TDM) or Frequency Division Multiplexing (FDM).

Figure 3D:
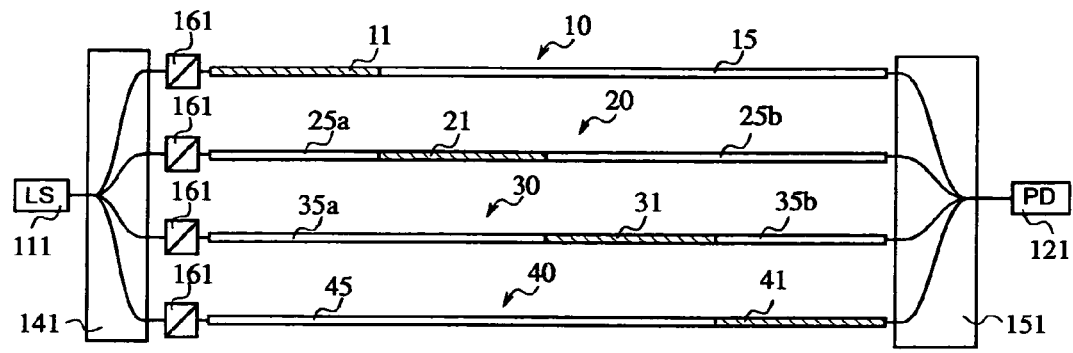

FIG. 3D shows an embodiment of the present invention in which a single light source 111 and a single photodetector are used 121. A 1×N optical splitter 141 (a series of 1×2 optical splitters may be used, as in FIG. 3B) is used to couple the single light source 111 to N optical fibers 10, 20, 30, 40 and an N×1 optical coupler 151 is used to combine the outputs of the optical fibers 10, 20, 30, 40 into a combined optical signal for the single photodetector 121. Preferably, an optical switch 161 is used to switch the optical signals in the N optical fibers 10, 20, 30, 40 to limit the photodetector 121 to receiving the optical signal from only one optical fiber at a time.

Figure 3E:
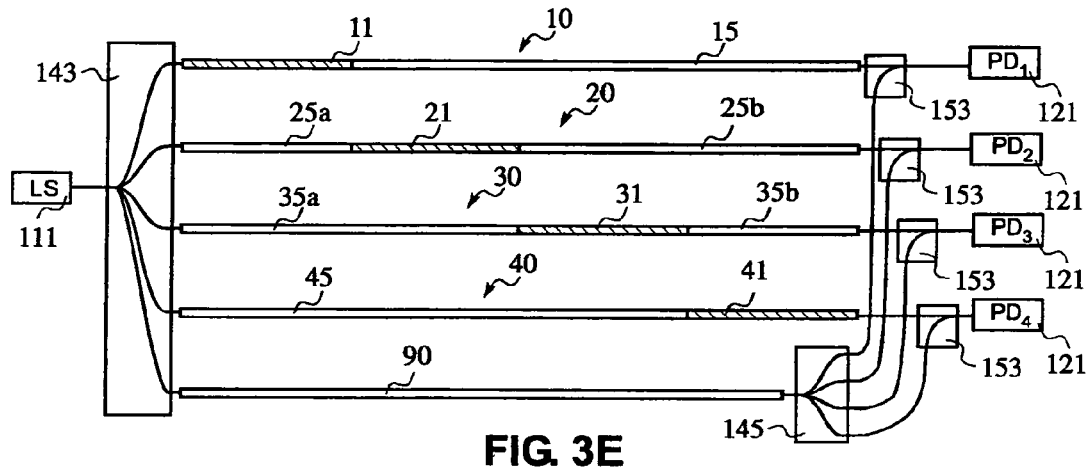

FIG. 3E shows an embodiment of the present invention in which N highly sensitive Mach-Zehnder interferometers are used to detect the change in the optical signal from a coherent light source. The embodiment comprises a single coherent light source 111 and N photodetectors 121. A 1×(N+1) splitter 143 splits the light from the coherent light source 111 into the N optical fibers 10, 20, 30, 40 and a reference optical fiber 90. The reference optical fiber 90 may have a length different than that of the N optical fibers 10, 20, 30, 40. The output of the reference fiber 90 is split by a 1×N splitter 145 and directed to N 2×1 optical couplers 153. Each 2×1 optical coupler 153 combines the output from one optical fiber 10, 20, 30, 40 and the reference optical fiber 90 and directs the combined signal to a photodetector 121. The combination of the 2×1 optical coupler 153 and the photodetector 121 acts as a Mach-Zehnder interferometer to detect changes in the optical signal directed through the optical fiber 10, 20, 30, 40. Other embodiments of the present invention may use other types of interferometers. For example, a sensing segment can comprise a component inside a Fabry-Perot cavity or become a branch of a Michelson interferometer.

Figure 3F:
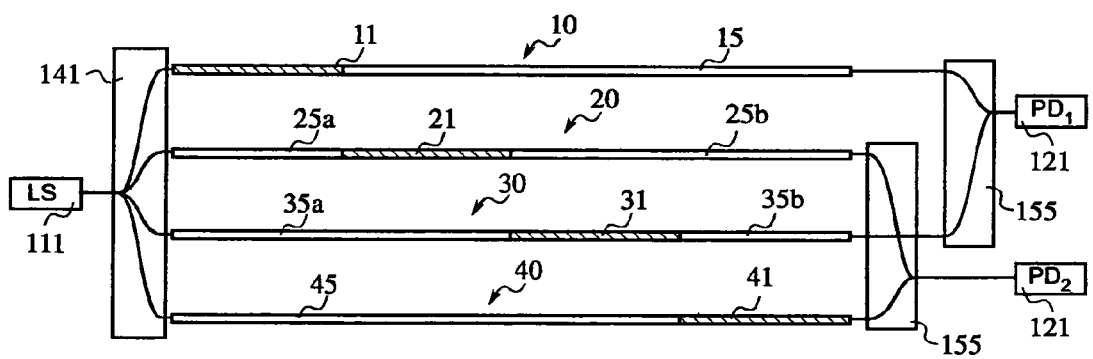

FIG. 3F shows an embodiment of the present invention in which changes in the optical signal from a coherent light source are detected, but no separate reference optical fiber is used. As shown in FIG. 3F, a 1×N splitter 141 is used to direct the light from a coherent light source 111 to N optical fibers 10, 20, 30, 40. The optical signals from a pair of non-adjacent optical fibers (10 and 30, or 20 and 40) are combined using 2×1 optical couplers 155 and the combined signal is directed to a photodetector 121. In this embodiment, one member of the pair serves as a reference for the other, for example fiber 30 serves as a reference for fiber 10 and fiber 40 serves as a reference for fiber 20. The embodiment in FIG. 3F uses only N/2 optical couplers and N/2 photodetectors. In this embodiment, it is assumed that the phase of the optical signal in non-adjacent segments does not change simultaneously, while the phase in adjacent segments may change. Hence, the output of each photodetector 121 will produce a signal that has a magnitude that reflects the strength of the optical signal in each fiber 10, 20, 30, 40 while the polarity of the photodetector output will indicate the fiber in which the change has occurred.

Another embodiment of the present invention uses balanced detection from two non-adjacent sensing segments on different fibers. This embodiment is intensity-based. However, since the information about the phase change is unavailable, this embodiment detects change in at least one of the fibers, but does not identify the affected segments.

As indicated above, alternative embodiments of the present invention may have the light sources and the light detectors located at the same end of the fibers, operating in reflection mode. FIG. 4A shows an embodiment of the present invention similar to the embodiment depicted in FIG. 3A. FIG. 4A shows four fibers 10, 20, 30, 40, where each fiber 10, 20, 30, 40 is illuminated by a dedicated light source 111 and the optical output is measured by a dedicated photodetector 121. However, optical circulators 171 are used to transmit light from each light source 111 into the fibers 10, 20, 30, 40. Reflection elements 173 disposed at the end of each fiber 10, 20, 30, 40 reflect light back through the fibers 10, 20, 30, 40 towards the optical circulators 171. The optical circulators then direct the reflected light to the photodetectors 121.

In the embodiment depicted in FIG. 4A, light is transmitted twice through the sensing segments 11, 21, 31, 41, once during forward transmission and once during reflected transmission. Hence, the embodiment depicted in FIG. 4A may provide twice the attenuation of light than that of a similar embodiment in which the light sources 111 and the photodetectors 121 are disposed at opposite ends of the fibers 10, 20, 30, and 40 (e.g., the embodiment depicted in FIG. 3A) and consequently provide increased sensitivity and an improved signal to noise ratio.

An alternative embodiment of the present invention similar to that shown in FIG. 3D is shown in FIG. 4B. FIG. 4B shows a single light source 111 and a single photodetector 121 coupled to a single optical circulator 171. The optical circulator 171 transmits light from the light source into an optical switch 175. The optical circulator 171 also transmits light from the optical switch 175 to the photodetector 121. The optical switch 175 directs light from the light source 171 to a selected one of the fibers 10, 20, 30, 40. The light then radiates down the selected fiber 10, 20, 30, 40, through the corresponding sensing segment 11, 21, 31, 41, and is reflected by the reflection element 173 disposed at the end of each fiber 10, 20, 30, 40 back through the corresponding analyte responsive segment 11, 21, 31, 41 and into the optical switch 175. The optical switch 175 is preferably controlled such that the timing relationship between light launched into a selected fiber 10, 20, 30 40 and the light received at the photodetector 121 is known (i.e., Time Division Multiplexing) so that the response seen at the photodetector 121 can be related to the corresponding fiber 10, 20, 30, 40. The embodiment shown in FIG. 4B also provides the advantage of effectively doubling the attenuation provided by the analyte responsive segments 11, 21, 31, 41.

Other embodiments of the present invention may adopt architectures similar to those shown in FIGS. 3B-3C and FIGS. 3E-3F, except that the light sources 111 and photodetectors 121 are placed at the same end of each fiber and a reflection element 173 is used at the opposite end of each fiber to reflect light back towards the end having the light sources 111 and photodetectors 121.

FIGS. 4A and 4B show a reflection element 173 disposed at the end of the fibers 10, 20, 30, 40. Those skilled in the art understand that the reflection element 173 may be provided by many elements and devices known in the art. Further, the reflection element 173 may be simply provided by terminating (e.g. cutting) the fiber 10, 20, 30, 40 or terminating the fiber 10, 20, 30, 40 and polishing and/or further shaping the fiber end to improve its reflection characteristics.

FIGS. 4A and 4B also show that the sensing segments 11, 21, 31 may be followed by the one or more lead portions 15, 25b, 35b and the reflection element 173 deployed at the distal end of each fiber 10, 20, 30, 40. However, according to some embodiments of the present invention, light transmission through the lead portions 15, 25b, 35b that are located on the other side of the sensing segments 11, 21, 31 from the light source 111 and photodetector 121 may not be required. Therefore, according to some embodiments of the present invention, the reflection element 173 may be simply disposed at the end of each sensing segment 11, 21, 31, 41, that is, immediately after each sensing segment 11, 21, 31, 41. This configuration may decrease the light attenuation caused by light propagation through the lead portions of the fibers.

In all of the foregoing descriptions and figures sensing segments are shown as being separate from lead portions before and after them. The means to separate analyte-sensing segments from lead portions is by connection such as by use of connectors or fusion connection or other connection means known in the art. However, alternative embodiments of the present invention may comprise a fiber in which the analyte-sensing segment is formed integrally with an adjacent lead portion albeit with some length of gradual transition due to the fiber manufacturing process to account for the transition from an analyte-sensing segment to a lead portion. It may ultimately be practical to apply sensing chemistry as a fiber is being manufacturing, which is likely to include a transition distance so that an optical fiber as contemplated by this description could be made from a single continuous fiber.

Therefore, in the broadest sense, an analyte-sensing segment may be either attached by connection or be integrally made with associated lead portions.

Figure 5:
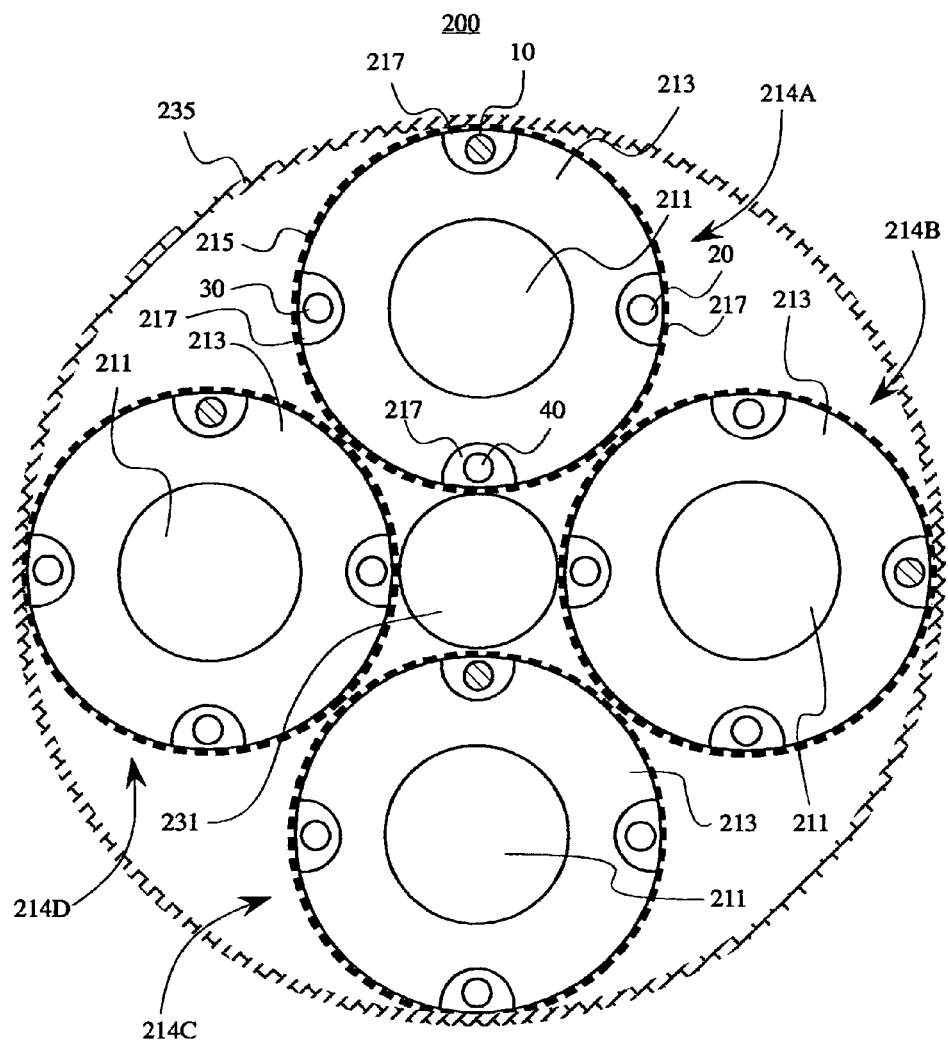
FIG. 5 is a schematic cross-sectional representation an embodiment of the present invention having a plurality of sensors supported by fiber carriers.

Fibers having analyte-sensing segments may be arranged in a cable assembly or harness as shown in FIG. 5. Specifically, FIG. 5 shows a cross-section of a cable assembly 200 having four segmented sensors such as those shown in FIGS. 1, 2A-2B, 3A-3F, 4A-4B. Each of the four fibers 10, 20, 30, 40 is disposed on a fiber carrier comprising a cylindrical slotted spine 213; A central strength member 211 may be embedded within the slotted spine 213 in case the material of the slotted spine 213 is not considered to be sufficiently strong. The slotted spine 213 is preferably constructed such that the fibers 10, 20, 30, 40 disposed within the slots 217 of the slotted spine 213 will be exposed to the environment in which analytes are to be detected. The combination of the slotted spines 213 and the fibers 10, 20, 30, 40 in the slots 217 defines a segmented cable or segmented optical fiber assembly also referred to as segmented sensor 214 in which the fibers 10, 20, 30, 40 are disposed lengthwise adjacently. A reticulated or foraminous covering 215 that permits passage of any analyte from the outside environment to the fibers 10, 20, 30, 40 may be used to retain the fibers 10, 20, 30, 40 in the slotted spine 213. An exemplary covering 215 is an open braid comprising glass yarn.

As shown in FIG. 5, the assembly 200 may dispose a plurality of segmented optical fiber assemblies 214 around a cable assembly central strength member 231. Hence, the cable assembly 200 may comprise multiple segmented cables 214A, 214B, 214C, 214D each of which may carry multiple fibers. Therefore the cable assembly 200 is made up of a plurality of segmented optical fiber assemblies that extend in a parallel bundle. Therefore, the cable assembly 200 may provide the capability to sense an analyte over a longer distance or with a finer distance resolution by reason of the greater number of sensing segments; and both benefits can be realized. The cable assembly 200 may also be used to detect multiple analytes by using analyte responsive segments that are responsive to different analytes. This enables a plurality of analyte sets of segmented optical fibers to be deployed where each analyte set has sensor segments responsive to a particular analyte and each analyte set is responsive to an analyte different from the other analyte sets so that surveillance for several different analytes can be established by segmented deployment. Preferably each of the segmented optical fiber assemblies 214 A-D is equipped with sensing segments in its optical fibers for the same analyte and each of them has sensing segments that differ from the others. That is, for example, segmented optical fiber assembly 214A may have optical fibers whose sensing segments are all responsive to a first analyte while segmented optical fiber assembly 214B has optical fibers whose sensing segments are all responsive to a second analyte. The cable assembly 200 may also be constructed such that the analyte responsive segments (indicated by the hatching in FIG. 5) appear at different rotational orientations of the slotted spines 213 by twisting the segmented cables around the strength member 231.

Figure 5D:
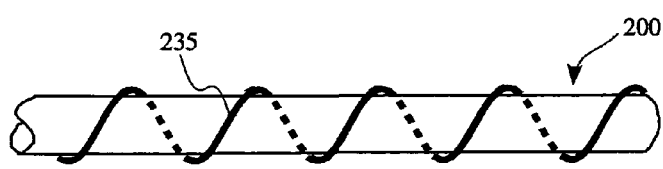
FIG. 5D shows an open wrap disposed around the fiber carrier.

In an exemplary embodiment, the cable assembly 200 depicted in FIG. 5 may have central strength members 211 comprising epoxy glass rods that each has a nominal diameter of 1.2 mm. The optical fibers 10, 20, 30, 40 may have outside nominal diameters of 250 µm and the fiber carriers 213 may have outside diameters of about 5.0 mm. The covering 215 such as braided glass yarn around each slotted spine 213 would then have an outside diameter of about 5.5 mm. The cable assembly central strength member 231 may also have a central core comprising an epoxy glass rod or a rod made of glass fibers. An open wrap 235 may then be used around all of the slotted spines 213 to hold all of the fibers and the segmented cables together. FIG. 5D shows how the open wrap 235 comprising, for example, a glass or plastic line may be wrapped lengthwise around the cable assembly 200.

Figure 5A:
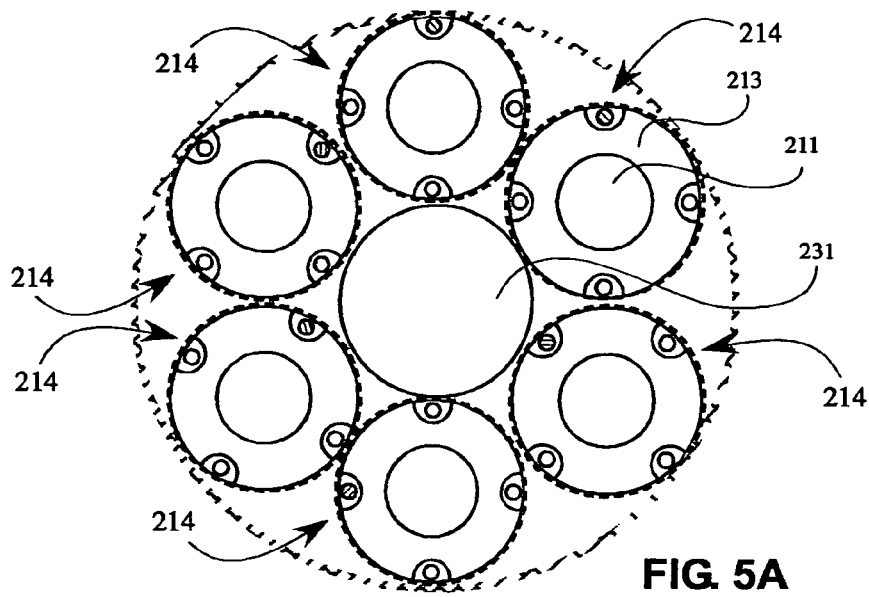
FIG. 5A shows that the embodiment depicted in FIG. 5 may be scaled to have additional fiber carriers.

The embodiment depicted in FIG. 5 may be scaled to have any number of segmented cables 214. FIG. 5A shows how the embodiment can be scaled to have six segmented cables 214.

In a preferred embodiment, each of the four segmented cables 214A-D in FIG. 5 is dedicated to a specific analyte such as hydrogen cyanide, hydrogen sulfide, chlorine gas, and nerve agent. In this case each optical fiber in one of the segmented cables (four segmented cables being illustrated) has a sensing segmented covering its own designated distance. The configuration of FIG. 5A can be similarly equipped with additional sensing cables for general environmental conditions such as temperature and humidity.

Figure 5B:
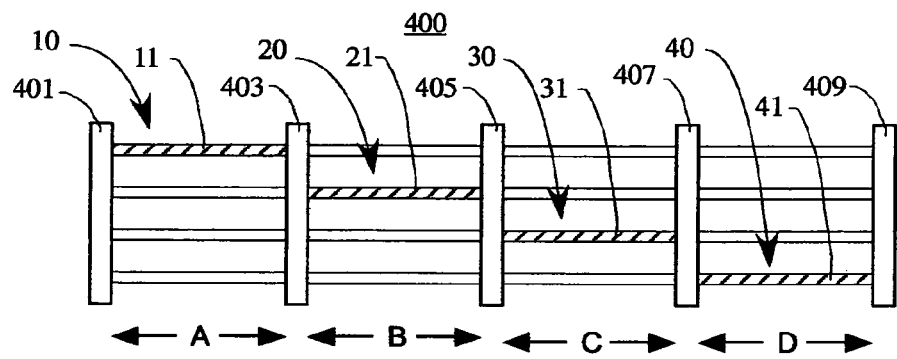
FIG. 5B shows schematically a connectorized configuration of the fiber carriers.

In a further embodiment of the invention as hereinbefore described, for each segmented cable (214 A-D in FIG. 5), each fiber's sensing segment is in a fiber length bounded by connectors, while the other fibers in that segmented cable are lead portions. This is illustrated in FIG. 5B in which a segmented cable 400 has connectors 401, 403, 405, 407 and 409. Fibers 10, 20, 30 and 40 run from connector 401 to connector 409 although they do so in discrete lengths A, B, C and D between the connectors. In each of the discrete lengths one of the fibers has its sensing segment as at 11, 21, 31, and 41, while the other fibers are lead portions. In this configuration, the sensing segments being substantially contiguous, a continuous distance can be under surveillance (it is discontinuous only to the extent of the distance occupied by the connectors), with the ability to determine if the analyte is present at one or more of the areas A, B, C, and D. In the case where a plurality of analytes is of interest, a plurality of segmented cables 400 is deployed, each being dedicated to a specific analyte.

Figure 5C:
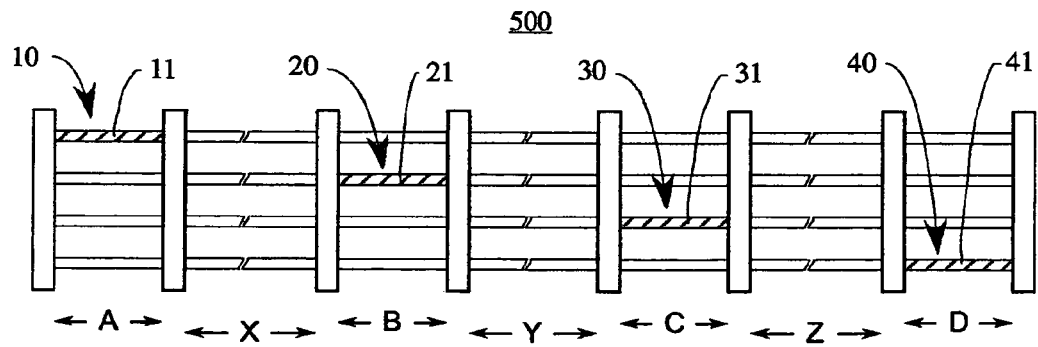
FIG. 5C shows a schematically a connectorized configuration of the fibers carriers with the sensing segments separated by non-sensing portions.

FIG. 5C shows a similar connectorized set-up 500 but with the sensing discrete lengths A, B, C and D being spaced-apart by any selected distance by the insertion of a wholly passive discrete length as, X, Y, and Z The connectorized configurations of FIGS. 5B and 5C can be applied to the arrangements of FIGS. 5 and 5A such that each segmented cable is bounded by connectors or splices, as 401 and 409 in FIG. 5A representing the ends of sensing cable 214A. Similarly each of the plurality of sensing cables 214 A-D would have ends bounded by connectors or splices with additional intermediate connectors representing each segmented distance. In the configurations of FIGS. 5-5C the sensing segments of each analyte set are grouped sequentially so that over a distance the first sensing segment for each analyte set is grouped spatially with the first sensing segment of the other analyte set(s) and so on for each sensing segment in spatial order.

Figure 6:
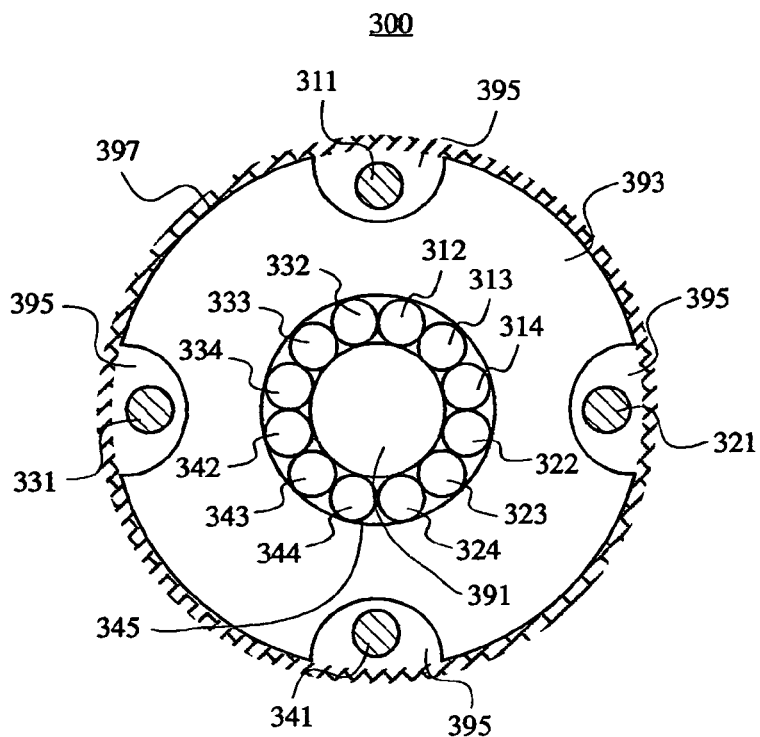
FIG. 6 shows a cross-section of an embodiment of the present invention having external analyte-sensing segments and embedded lead portions.

In another embodiment for use in a system set up for surveillance for a plurality of analytes, analyte sets of segmented fibers, each analyte set having sensing segments for a particular analyte are installed on a fiber carrier. In general fiber carriers have a portion on which the sensing segments are carried such as a surface that is available to be deployed so that it will encounter an analyte the presence of which it is in surveillance for and there is also a portion for carrying the lead portions of the fibers. The latter portion can be a surface or conduit that is located on the fiber carrier in a place that is convenient to carry all the lead portions and it need not be and preferably is not positioned to encounter the analyte but rather is positioned to allow a clear and unobstructed deployment of the sensing segments. In one embodiment, the fiber carrier has an external structure on which the first sensing segments, in sequential order, for each analyte set are disposed adjacently. The fiber carrier also has a passive structure (surface or conduit or the like) on which all the lead portions are disposed. The external structure is exposed to the environment in order that the sensing segments be exposed to an analyte when present while the passive structure can be hidden or on a reverse side where exposure to the analyte is irrelevant. FIG. 6 depicts an example of this embodiment. FIG. 6 depicts a cross-section of an assembly 300 comprising a slotted fiber carrier 393 with lead fiber portions 312, 313, 314, 322, 323, 324, 332, 333, 334, 342, 343, 344 contained inside the slotted fiber carrier 393 in an interior conduit 345 and sensing segments 311, 321, 331, 341 located in slots 395 on the external structure 399 of the fiber carrier 393. A braid 396 or other means can be used to retain the sensing segments in the slots 395. The embodiment shown in FIG. 6 may have a smaller diameter than the embodiment shown in FIG. 5, since the embodiment of FIG. 6 only uses a single fiber carrier for surveillance for a plurality of analytes. Note also that the embodiment of FIG. 6 allows the sensing segments 311, 321, 331, 341 to be more completely exposed to the ambient environment, which may facilitate the detection of chemical agents (i.e., analytes) and decrease the response time. Although slots have been shown for retaining and positioning the fibers on the carrier periphery, it will be apparent to those skilled in the art that other retaining means could be employed, for example, spaced apart pairs of posts could be embedded or molded into the carrier or simple ties could be used to secure the fibers.

Figure 7:
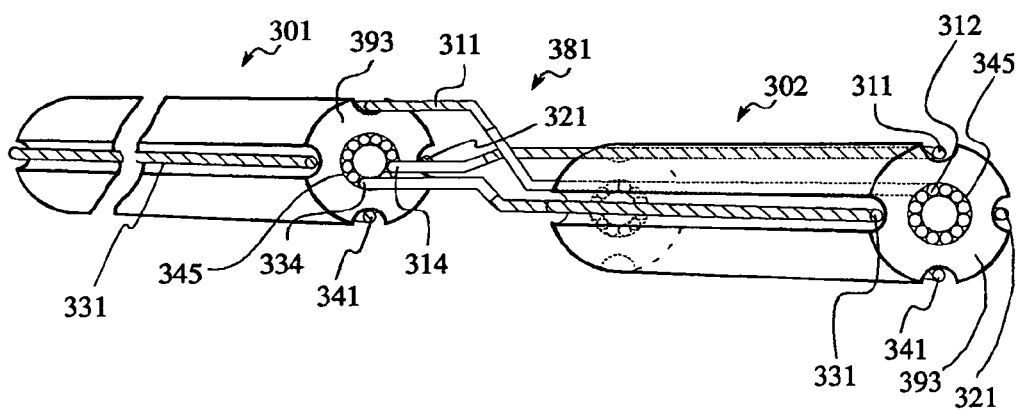
FIG. 7 shows a fiber carrier and fiber configuration according to an embodiment of the invention.

FIG. 7 depicts how the transition from a sensing segment 311 located on the periphery of the slotted spine carrier 393 to an internally located lead portion 312 may be handled. FIG. 7 depicts a first fiber assembly 301 coupled to a second fiber assembly 302, each of which has the structure of the assembly 300 shown in FIG. 6. FIG. 7 shows a sensing segment 311 located on the periphery of the first fiber assembly 301 coupled to a lead portion 312 located within the conduit 345 in the slotted spine carrier 393 of the second fiber assembly 302. Similarly, FIG. 7 shows a first lead portion 334 and a second lead portion 314, both located within the conduit 345 in the slotted spine carrier 393 of the first assembly 301, coupled to a sensing segment 331 and a second sensing segment 311, respectively, both located on the periphery of the second assembly 302.

As shown in FIG. 7, only the sensing segment (depicted by hatching) of each fiber is exposed, while the remainder of the fiber is buried within the slotted spine carrier 393 in the conduit 345. Thus, FIG. 7 depicts four simultaneously sensing fiber segments, each responsive to a different sensing chemistry.

It is to be noted that the first and second fiber assemblies 301, 302 are linearly adjacent so that the sensing segments on the surface of first assembly 301 are exposed the whole length of first assembly 301; and then their lead portions are concealed in the conduit 345 in the second assembly 302. Additional such assemblies can be fitted so that sensing segments for each sensing chemistry on different fibers are exposed on each assembly thereby allowing for location of analytes. Hence, fiber assemblies of optimum length may be connected together by standard optical connectors (represented by 381 in FIG. 7). For example, each fiber assembly may be a certain length and connected together in groups of four to provide a sensor having a length additive of their individual lengths (disregarding small distances occupied by connectors).

Figure 8:
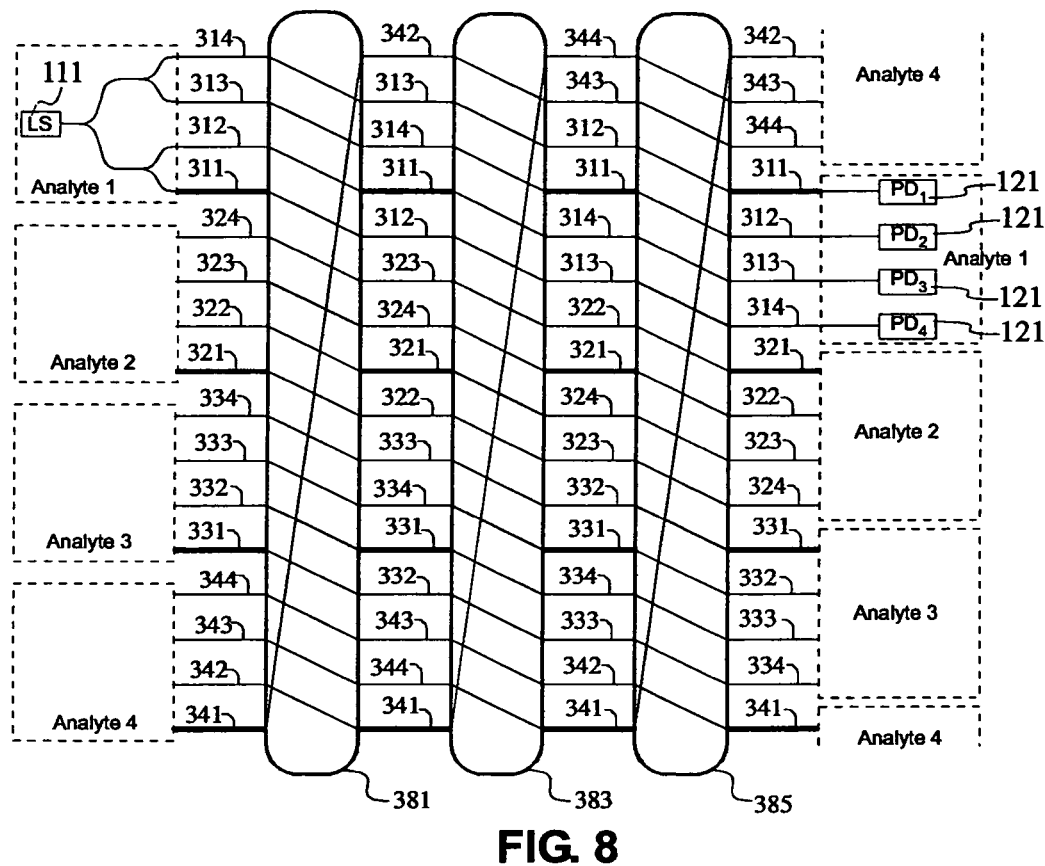
FIG. 8 is a schematic representation of the organization of sensors of the multi-carrier sensor system of FIG. 7.

FIG. 8 shows schematically the organization of a sensor of the type shown in FIG. 7. Specifically, the schematic of FIG. 8 is based on the assumption that four different sensing chemistries are used with segments 311, 321, 331 and 341 of FIG. 7. Sixteen fibers are required for four segmented sensors for four analytes. Connector 381 of FIG. 8 corresponds in position to the space between assembly 301 and assembly 302 of FIG. 7. FIG. 8 shows that the analyte-sensing segments for the first sensing chemistry are denoted as element 311. The left most fiber assembly shown in FIG. 8 corresponds to the first fiber assembly 301 shown in FIG. 7. FIG. 8 shows that the analyte-sensing segment 311 in this left most assembly couples through the connector 381 to lead portions 312 in the next fiber assembly. This next fiber assembly corresponds to the second fiber assembly 302 in FIG. 7. FIG. 7 shows that the lead portion 312 is embedded within the conduit 345. Two additional connectors, connector 383 and connector 385, are required to connect the four fiber assemblies into a complete four segment sensor. For example, each fiber assembly may be 20 meters, so that the total length of the sensor is 80 meters.

The different analyte sets of FIGS. 6-9 are like those of FIGS. 5-5C sequentially grouped so that along a distance over which they are deployed a spatially first sensing segment for each group is on the same fiber carrier and consequently is surveilling the same partial length of the distance under surveillance and similarly the next sensing segments in spatial order for each analyte set are grouped and so on for all the sensing segments, in spatial order.

In an experimental set up, four chemistries were used to sense the presence of four different analytes, each requiring light of a different wavelength. The blocks (outlined) to the left as viewed in FIG. 8 represent the optical light source input; the blocks to the right represent the corresponding photodetectors measuring responses to individual chemistries.

Advantageously, the optical fibers are twisted by a relative rotation of the carriers with respect to one another to avoid possible stress on the system if the apparatus is placed along arcuate paths. This rotation is represented by the position of the optical fibers in the space between the first fiber assembly 301 and the second fiber assembly 302 of FIG. 7.

Figure 10:
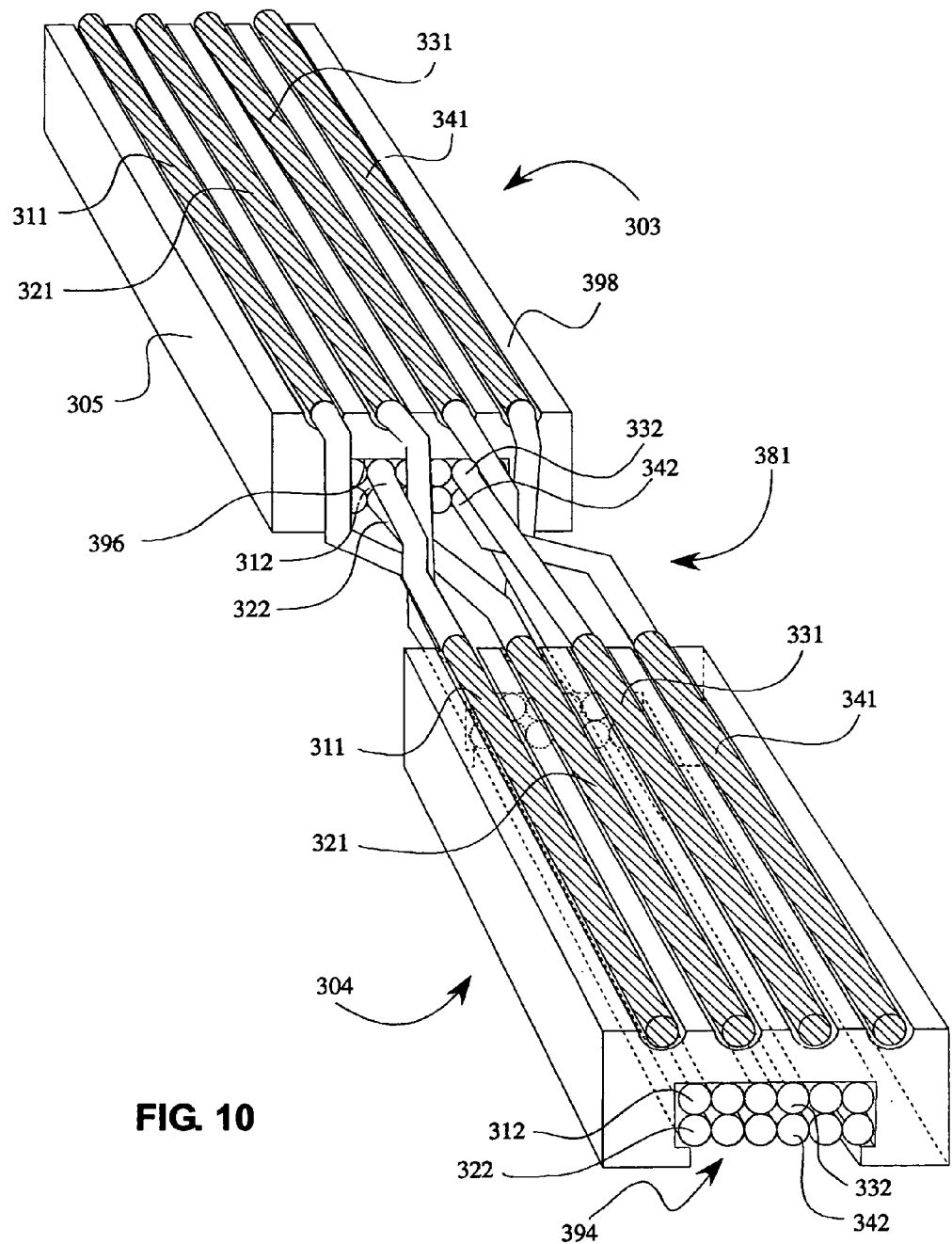
FIG. 10 shows a fiber carrier and fiber configuration according to an embodiment of the invention.

Fiber carriers according to embodiments of the present invention are not limited to carriers with circular cross-sections. FIG. 10 shows an alternative embodiment of the present invention with a fiber carrier having a non-circular cross-section. FIG. 10 shows a first fiber assembly 303 coupled to a second fiber assembly 304, each assembly 303, 304, having a fiber carrier 305 with a rectangular cross-section. The fiber carrier 305 has an external structure 398 on which the analyte-responsive segments 311, 321, 331, 341 are disposed. The external structure 398 proves for exposure of the analyte-responsive segments 311, 321, 331, 341 to the environment in which analytes are to be detected. Lead portions 312, 322, 332, 342 are disposed in a passive structure 394 which is a cavity on the bottom of the fiber carrier 305. Other embodiments according to the present invention may disposed the passive structure on a surface of the fiber carrier 305. While FIG. 10 shows a fiber carrier 305 with a rectangular cross-section, other fiber carriers of other embodiments according to the present invention may have cross-sections with different shapes.

FIG. 10 also shows the transitions from the analyte-responsive segments 311, 321, 331, 341 to the lead portions 312, 322, 332, 342. FIG. 10 shows the analyte-responsive segment 311 of the first assembly 303 coupled to lead portion 312 of the second fiber assembly 304. Similarly, FIG. 7 shows the portion 312 of the first assembly 303 coupled to the analyte-responsive segment 311 of the second assembly 302. The coupling of segments of the first assembly 303 and the second assembly 304 may be accomplished with coupling means 381 known in the art, such as fiber couplers connectors, fiber bonding, etc.

Figure 11:
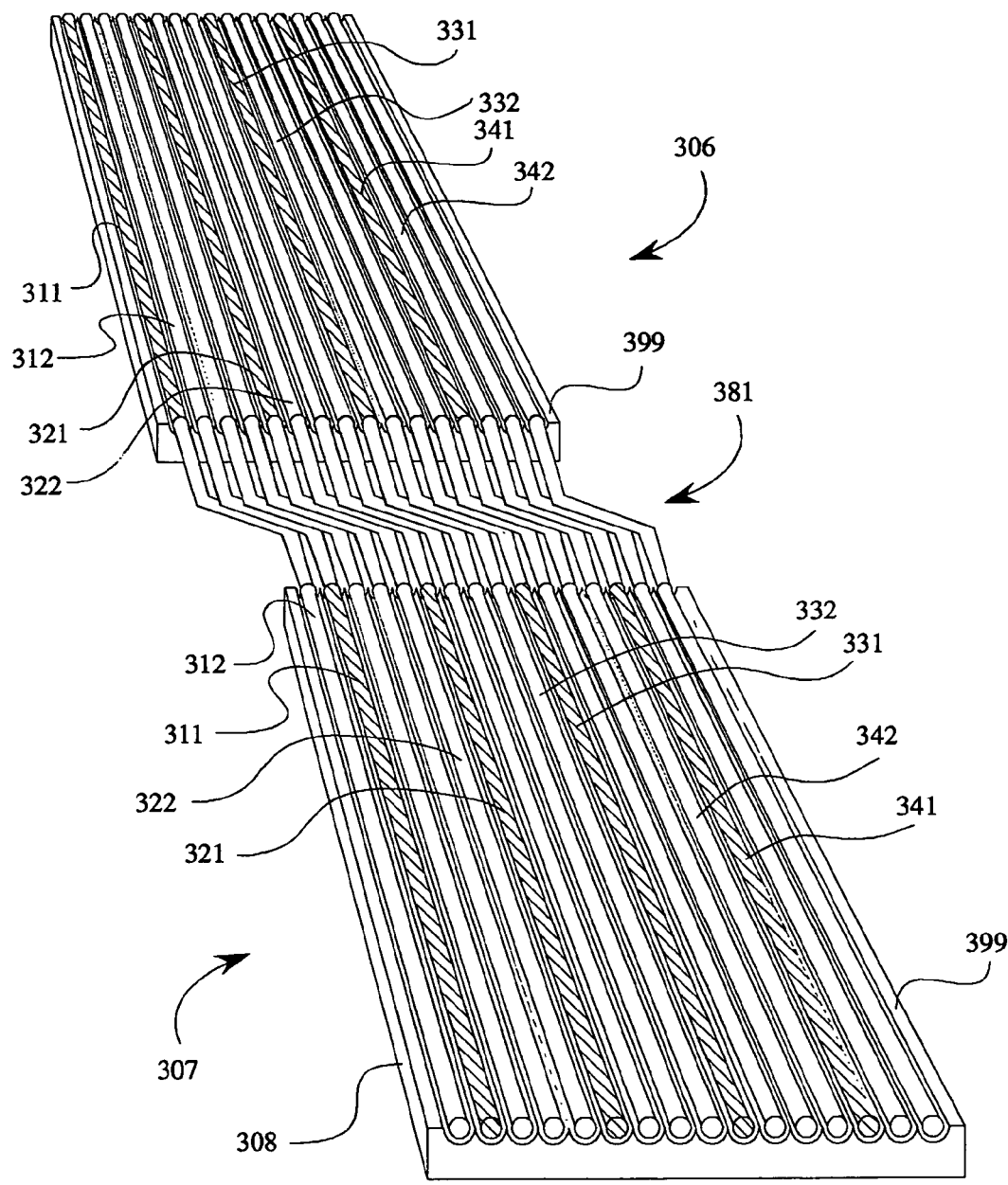
FIG. 11 shows a fiber carrier and fiber configuration according to an embodiment of the invention.

FIG. 11 shows an alternative embodiment of the present invention with a ribbon-like fiber carrier. FIG. 11 shows a first fiber assembly 306 coupled to a second fiber assembly 307, each assembly 306, 306, having a fiber carrier 308 generally shaped like a ribbon. The fiber carrier 308 has an external structure 399 on which both the analyte responsive segments 311, 321, 331, 341 and the non-analyte-responsive segments 312, 322, 332, 342 are disposed. The analyte responsive segments 311, 321, 331, 341 and the non-analyte-responsive segments 312, 322, 332, 342 are disposed generally parallel to each other on the external structure 399. The external structure 399 proves for exposure of the analyte responsive segments 311, 321, 331, 341 to the environment in which analytes are to be detected and also provides a carrying surface for the non-analyte responsive segments 312, 322, 332, 342.

FIG. 11 also shows the transitions from the analyte responsive segments 311, 321, 331, 341 to the non-analyte responsive segments 312, 322, 332, 342. FIG. 11 shows the analyte responsive segment 311 of the first assembly 303 coupled to the non-analyte responsive segment 312 of the second fiber assembly 304. Similarly, FIG. 11 shows the non-analyte responsive segment 312 of the first assembly 303 coupled to the analyte responsive segment 311 of the second assembly 302. The coupling of segments of the first assembly 306 and the second assembly 307 may be accomplished with coupling means 381 known in the art, such as fiber couplers, fiber bonding, etc.

FIG. 11 shows the analyte responsive segments 311, 321, 331, 341 spaced apart from each other by the non-analyte-responsive segments 312, 322, 332, 342, but other embodiments may have all of the analyte responsive segments positioned next to each other or distributed arbitrarily in any position on the external structure 399. Further, while FIG. 11 shows the analyte responsive segments 311, 321, 331, 341 at different positions on the first assembly 306 and the second assembly 307, other embodiments may have the analyte responsive segments 311, 321, 331, 341 at the same positions on each fiber assembly. The coupling means 381 would then provide the transition from an analyte responsive segment to a non-analyte responsive segment. Hence, an arbitrarily long ribbon carrier could be manufactured with both analyte responsive and non-analyte responsive fibers on it, which would then be cut into shorter fiber assembly segments (similar to that described in regard to FIG. 6). The fiber assembly segments could then be coupled by coupling means to provide an embodiment of the present invention similar to that shown in FIG. 11

An embodiment of the present invention may be fabricated by producing a long single harness (e.g. 5000 meters) of the type depicted in FIG. 6. That is, the embodiment comprises a braided harness with analyte sensing fibers on the outside of a fiber carrier and low attenuation lead fiber portions embedded within the carrier. The braided harness can then be cut into the appropriate sensing lengths. The length may be determined by the attenuation of the sensing fiber segments. Standard fiber optic connectors may then be used to connect together the segments.

As described above, fiber optic sensors organized in a segmented arrangement as shown in the figures described above may be used to detect multiple types of analytes. For example, a first set of fibers may be coated with a coating normally comprising a cladding including a colorimetric indicator for sensing hydrogen cyanide. A second set of fibers may then be coated with a coating including an indicator for sensing chlorine gas. A third set of fibers may detect hydrogen sulfide and a fourth set, a nerve agent. Hence, the combination of fibers could detect all of hydrogen cyanide and chlorine gas, hydrogen sulfide and a nerve agent in a linearly segmented system. Preferably, the coatings are curable using either ultra violet light or heat. The coatings may then be cured as they are applied to optical cores as the cores are drawn. Exemplary coatings include silicones and acrylates. According to embodiments of the present invention, the (segmented) sensors may be packaged as shown in FIGS. 5 and 5A or 6 and 7.

The decreased attenuation provided by an embodiment of the present invention is shown by examining typical optical fibers known in the art. Typically, chemically sensitive optical fiber may have attenuation on the order of 1 dB/m, while low attenuation multimode optical fiber (not chemically sensitive) may have attenuation as low as 0.04 dB/m. Each optical fiber of the four optical fiber embodiment (described above) requires three additional optical connectors with each connector having a loss of about 0.1 dB. In the array shown in FIG. 1, a 1:4 optical splitter is used to launch the light into the four separate fibers and a 4:1 optical combiner is used to combine the light for application to the photodetector. The optical splitter and the optical combiner are each estimated to provide an additional 1 dB of loss.

Hence, the total optical losses through a single fiber in the embodiment shown in FIG. 1 are estimated as 20 m×1 dB/m (sensing segment loss)+60 m×0.04 dB/m (lead segment loss)+3×0.1 dB (connector loss)+2×1 dB (splitter/combiner loss)=24.7 dB. Hence, the total optical power attenuation from the source to the photodetector is estimated as 24.7 dB. On the other hand, if the entire optical fiber is chemically sensitive fiber as is known in the art, the total attenuation is estimated as 80 m×1 dB/m=80 dB. Therefore, the embodiment depicted in FIG. 1 may provide 55.3 dB less attenuation than a sensing system using a single chemically sensitive optical fiber.

An embodiment of the present invention may be used to provide for continuous chemical surveillance over a desired distance. As shown in FIG. 2A, a structure having multiple optical fibers may be deployed (FIG. 2A shows four fibers 10, 20, 30, 40, but more or fewer fibers may be used in accordance with the present invention), where each optical fiber has a sensing segment. To provide for continuous chemical surveillance, the sensing segments for a given chemistry should be positioned such that the segments are offset which may include contiguous, or overlapping. Hence, the presence of an analyte at any position along the structure may be detected, and spatially resolved within the distance covered by one or more segments that respond to its presence, while maintaining the low loss characteristics described above. This type of arrangement is particularly useful to determine the presence of an analyte at a particular sensing segment in place at a known location over otherwise undifferentiated distances such as for perimeter surveillance.

Figure 9:
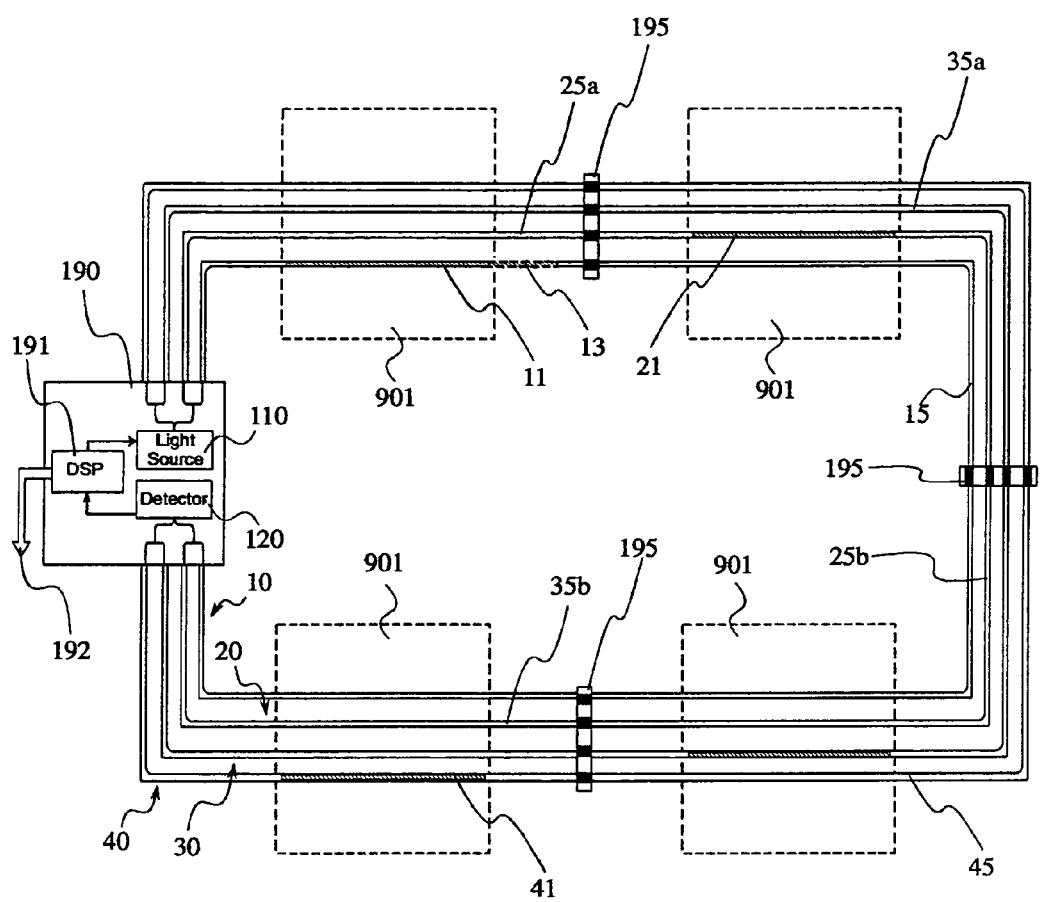
FIG. 9 shows an embodiment of the present invention that provides for analyte detection in selected areas.

Another embodiment of the present invention provides for chemical surveillance at selected spaced-apart positions along the length of the detecting structure (see FIG. 9). As shown in FIG. 2B, a structure having multiple optical fibers may be deployed (FIG. 2B shows four fibers 10, 20, 30, 40, but more or fewer fibers may be used in accordance with the present invention), where each optical fiber has a sensing segment. However, unlike the structure depicted in FIG. 2A, the sensing segments may not be contiguous or overlapping. Instead, the sensing segments are spaced-apart, positioned at those intervals at which the detection of an analyte is desired, while intervening positions use the low loss lead fiber portion discussed above. Hence, the sensing segment in one optical fiber may be spaced-apart from the sensing segments in the other optical fibers. The length of the sensing segments may differ. Hence, the presence of an analyte at selected positions can be detected, while maintaining the low loss characteristics described above. This is particularly useful in structures where sensing segments can be located at separate spaced-apart locations such as windows, doors, air intakes and the like openings in the structure where an attack may be targeted.

FIG. 9 depicts an embodiment of the present invention used for detecting analytes in separate spaced-apart physical locations. A detecting structure comprising four fibers 10, 20, 30, 40 is disposed through four separate areas 901. The separate areas 901 may be separate rooms, portions of rooms, separate buildings, etc. FIG. 9 shows the sensing segments 11, 21, 31 and 41 extending throughout an entire dimension of separate areas 901, but the sensing segments may extend for only a portion of the areas 901 or may extend past the areas 901, as illustrated by segment 13. The fibers may be fabricated in structures such as those shown in FIGS. 5, 5A or 6 and may be coupled together with optical connectors 195. A control element 190, comprising a light source 110 and a photodetector 120 both coupled to a processor 191, transmits light into the fibers 10, 20, 30, 40 and receives light from the fibers 10, 20, 30, 40. The processor 191 may be a digital signal processor that both controls the light generated by the light source 110 and processes the electrical signals generated by the photodetector 120. The control element 190 provides an external output 192, which indicates whether an analyte has been sensed by any of the fibers 10, 20, 30, 40 and, therefore, indicates the location of the sensed analyte. As discussed above, an alternative embodiment may have the light source 110 and the photodetector 120 disposed at the same end of the fibers 10, 20, 30, 40 and a reflection element disposed at the distal end of the fibers.

What has been described is considered merely illustrative of the invention. Those skilled in the art are competent to make variations and modifications of the illustrations herein still within the spirit and scope of the invention as claimed hereinafter.

What is claimed is:

1. An apparatus for analyte surveillance over a distance comprising;
    a plurality of optical fibers, each optical fiber of the plurality of optical fibers having a distributed intrinsic chemical fiber optic sensing segment responsive to the same analyte and each sensing segment having a length and being disposed in sequential lengthwise offset relationship over a distance to provide a substantially continuous analyte sensing length over the distance.

2. The apparatus as claimed in claim 1 wherein each optical fiber has one or more lead portions that have low attenuation relative to the attenuation of the sensing segments.

3. The apparatus as claimed in claim 1 wherein the number of optical fibers in the plurality of optical fibers equals N and the distance equals L and each sensing segment has a length equal to L/N.

4. The apparatus as claimed in claim 1 wherein said plurality of optical fibers defines a first analyte set of a plurality of optical fibers and further comprising one or more additional analyte sets of a plurality of optical fibers, each of said first and additional analyte sets having sensing segments that are disposed in sequential lengthwise offset relationship over a distance and being responsive to an analyte that is different from that of any other analyte set.

5. The apparatus as claimed in claim 1 further comprising;
    an optical energy source disposed to transmit light into the plurality of optical fibers, and
    an optical energy detector coupled to the plurality of optical fibers to receive light from the plurality of optical fibers.

6. The apparatus as claimed in claim 4 wherein the sensing segments of each analyte set are spatially disposed in sequential groups.

7. The apparatus as claimed in claim 5 wherein the optical energy source and the optical energy detector are coupled to proximal ends of the plurality of optical fibers with and reflective elements being disposed at distal ends of the plurality of optical fibers.

8. The apparatus as claimed in claim 5, wherein the optical energy source is disposed at proximal ends of the plurality of optical fibers and the optical energy detector is disposed at distal ends of the plurality of optical fibers.

9. The apparatus as claimed in claim 5 wherein the optical energy source is selected from the group consisting of,
a plurality of light sources;
one or more light sources and one or more optical splitters coupled to the one or more light sources;
one or more light sources and one or more optical splitters coupled to receive light from the one or more light sources and a plurality of optical switches coupled to the one or more optical splitters to receive light from the one or more optical splitters.

10. The apparatus as claimed in claim 5 wherein the optical energy detector comprises a plurality of light detectors, or one or more optical combiners and one or more light detectors disposed to receive light from the one or more optical combiners.

11. The apparatus as claimed in claim 5 further comprising one or more reference fibers and the optical energy source comprises one or more coherent light sources coupled to at least one light source splitter, wherein the at least one light source splitter transmits light to the plurality of optical fibers and the one or more reference fibers, and the optical energy detector comprises: a plurality of light detectors; a plurality of optical combiners, each optical combiner having an output coupled to a corresponding one light detector of the plurality of light detectors, a first input coupled to a corresponding one optical fiber of the plurality of optical fibers, and a second input disposed to receive light from the one or more reference fibers; and one or more reference fiber splitters coupled to receive light from the one or more reference fibers and to transmit light to the second inputs of the optical combiners.

12. The apparatus as claimed in claim 5 wherein the optical energy source comprises one or more coherent light sources coupled to at least one light source splitter and the at least one light source splitter transmits light to the plurality of optical fibers and the optical energy detector comprises a plurality of light detector and optical combiner combinations, wherein the optical combiner of each combination has a first input coupled to a first optical fiber of the plurality of optical fibers and a second input coupled to a second optical fiber of the plurality of optical fibers and an output coupled to a light detector.

13. The apparatus as claimed in claim 5 further comprising a processor coupled to the optical energy source and the optical energy detector wherein the processor produces an output based on detection of an analyte including identification of one or more sensing segments that responded to an analyte.

14. The apparatus as claimed in claim 6 further comprising;
each optical fiber having at least one lead portion extending from a terminal end of the sensing segment having low attenuation relative to the attenuation of the sensing segment; and
a plurality of sequentially disposed fiber carriers having a sensor support structure and a lead support structure and the sensing segments of each analyte set are spatially disposed in sequential groups on the sensor support structure and the lead portions of each set are disposed on the lead support structure whereby the fiber carrier may be deployed so that the sensor support structure can be exposed to an analyte whose presence is under surveillance and the lead support structure need not be disposed for exposure to analytes.

15. The apparatus of claim 6 further comprising a plurality of elongate fiber carriers disposed sequentially, each fiber carrier having an internal conduit and an external structure and each optical fiber having one or two lead portions extending from a single one of or both terminal ends of the sensing segments each of the plurality of fibers being fitted to the plurality of fiber carriers such that its sensor segment is retained on the external structure of one fiber carrier and the one or both lead portions are carried in the internal conduits of the one or more other fiber carriers whereby the sensing segment of each of the fibers is on the external structure of one fiber carrier and all lead portions of the fibers are in the conduit or conduits of one or a plurality of other fiber carriers whereby the fiber carriers having sensing segments on their external structure may be disposed at each of a plurality of desired locations thereby to be in surveillance at the plurality of locations for an analyte or analytes.

16. The apparatus as claimed in claim 8 wherein the optical energy source comprises a plurality of light sources, at least one light source for each optical fiber, and the optical energy detector comprises a plurality of photodetectors, at least one photodetector for each optical fiber, and each optical fiber has at least one light source and at least one photodetector coupled to the proximal end of the optical fiber through one of the one or more optical circulators.

17. The apparatus as claimed in claim 8 wherein the optical energy source comprises one or more light sources and the optical energy detector comprises one or more photodetectors and one or more optical switches couple the one or more optical circulators to the proximal ends of the plurality of optical fibers.

18. The apparatus as claimed in claim 14 further comprising optical connectors or optical splices coupling the portions of optical fibers disposed on each fiber carrier to the portions of optical fibers in an adjacent fiber carrier.

19. The apparatus as claimed in claim 15 wherein the fiber carrier is circular in cross section and the outside periphery is the external structure and having a conduit in it that is the passive structure whereby the sensing segments are disposed on the outside periphery and the lead portions are disposed in the conduit.

20. The apparatus of claim 15 wherein a sensing segment of each of the plurality of fibers is on the external structure of each fiber carrier, sequentially.

21. The apparatus of claim 15 wherein intermediate fiber carriers have only lead portions in their conduits so that the fiber carriers with sensing segments are separated by any selected number of intermediate fiber carriers that have no sensing segments.

22. The apparatus of claim 21 wherein fiber carriers having sensing segments are of a predetermined length appropriate to a location for surveillance and one or more intermediate fiber carriers having only lead portions in the conduit thereof are of a length to effect connection of the fiber carriers having sensing segments.

23. The apparatus of claim 21 further comprising;
an optical energy source disposed to transmit light into the plurality of optical fibers, and
an optical energy detector coupled to the plurality of optical fibers to receive light from the plurality of optical fibers.

24. An apparatus for analyte surveillance at selected locations comprising;
a plurality of optical fibers, each optical fiber of the plurality of optical fibers having a distributed intrinsic chemical fiber optic sensing segment for the same analyte the sensing segments each having a length and being disposed in sequential spaced apart relationship over a distance to provide a sensing segment at each of selected locations whereby the presence of the analyte may be detected at one or more of the selected locations at which one or more sensing segments respond to the analyte presence by detecting the response of the one or more sensing segments to the presence of the analyte.

25. The apparatus as claimed in claim 24 further wherein said plurality of optical fibers defines a first analyte set of a plurality of optical fibers and further comprising one or more additional analyte sets of a plurality of optical fibers each of said first and additional analyte sets having sensing segments responsive to an analyte that is different from that of any other set and being disposed in sequential spaced apart groups at the selected locations.

26. The apparatus as claimed in claim 24 wherein each optical fiber has one or more lead portions that have low attenuation relative to the attenuation of the sensing segments.

27. The apparatus as claimed in claim 24 further comprising;
an optical energy source disposed to transmit light into the plurality of optical fibers, and
an optical energy detector coupled to the plurality of optical fibers to receive light from the plurality of optical fibers.

28. The apparatus as claimed in claim 25 further comprising;
each optical fiber having at least one lead portion extending from a terminal end of the sensing segment having low attenuation relative to the attenuation of the sensing segment; and
a plurality of sequentially disposed fiber carriers having a sensor support structure and a lead support structure and the sensing segments of each analyte set are spatially disposed in sequential groups on the sensor support structure at the selected locations and the lead portions of each set are disposed on the lead support structure whereby the fiber carriers may be deployed so that the sensor support structure can be exposed to an analyte whose presence is under surveillance at the selected locations and the lead support structure need not be disposed for exposure to analytes.

29. The apparatus of claim 25 further comprising a plurality of elongate fiber carriers disposed sequentially, each fiber carrier having an internal conduit and an external structure and each optical fiber having one or two lead portions extending from a single one of or both terminal ends of the sensing segments each of the plurality of fibers being fitted to the plurality of fiber carriers such that its sensor segment is retained on the external structure of one fiber carrier and the one or both lead portions are carried in the internal conduits of the one or more other fiber carriers whereby the sensing segment of each of the fibers is on the external structure of one fiber carrier and all lead portions of the fibers are in the conduit or conduits of one or a plurality of other fiber carriers whereby the fiber carriers having sensing segments on their external structure may be disposed at each of a plurality of desired locations thereby to be in surveillance at the plurality of locations for an analyte or analytes.

30. The apparatus as claimed in claim 27 wherein the optical energy source and the optical energy detector are coupled to proximal ends of the plurality of optical fibers with and reflective elements being disposed at distal ends of the plurality of optical fibers.

31. The apparatus as claimed in claim 27 wherein the optical energy source is disposed at proximal ends of the plurality of optical fibers and the optical energy detector is disposed at distal ends of the plurality of optical fibers.

32. The apparatus of claim 29 wherein a sensing segment of each of the plurality of fibers is on the external structure of each fiber carrier, sequentially.

33. The apparatus of claim 29 wherein intermediate fiber carriers have only lead portions in their conduits so that the fiber carriers with sensing segments are separated by any selected number of intermediate fiber carriers that have no sensing segments.

34. The apparatus of claim 33 further comprising; an optical energy source disposed to transmit light into the plurality of optical fibers, and an optical energy detector coupled to the plurality of optical fibers to receive light from the plurality of optical fibers.

35. The apparatus as claimed in claim 34 wherein the optical energy source and the optical energy detector are coupled to proximal ends of the plurality of optical fibers with and reflective elements being disposed at distal ends of the plurality of optical fibers.

36. The apparatus as claimed in claim 34 wherein the optical energy source is disposed at proximal ends of the plurality of optical fibers and the optical energy detector is disposed at distal ends of the plurality of optical fibers.

37. A method for sensing the presence of one or more analytes, the method comprising:
disposing a plurality of distributed intrinsic chemical optical fiber sensing segments at desired locations;
providing lead portions to transmit optical energy into the sensing segments; and
providing lead portions to receive optical energy from the optical fiber sensing segments the lead portions having low attenuation relative to the attenuation of the sensing segments;
wherein the sensing segments, the optical fiber input segments, and the lead segments comprise a plurality of optical fibers disposed lengthwise adjacently and each optical fiber has one sensing segment that is offset from the sensing segments of the adjacent optical fibers to provide a substantially continuous analyte-sensing length over a distance.

38. The method as claimed in claim 37 wherein the optical fiber sensing segments are disposed on external structure of one or more fiber carriers.

39. The method as claimed in claim 38 wherein one or more of the optical fiber input segments and/or one or more of the optical fiber output segments are embedded within at least one of the fiber carriers.

40. The method as claimed in claim 37, wherein the number of optical fibers in the plurality of optical fibers equals N and the distance equals L and each sensing segment has a length equal to L/N.

41. A method for sensing the presence of one or more analytes, the method comprising:
disposing a plurality of distributed intrinsic optical fiber chemical sensing segments at desired locations;
providing lead portions to transmit optical energy into the sensing segments; and
providing lead portions to receive optical energy from the optical fiber sensing segments the lead portions having low attenuation relative to the attenuation of the sensing segments;
wherein the sensing segments, the optical fiber input segments, and the lead segments comprise a plurality of optical fibers disposed lengthwise adjacently, wherein each optical fiber has one or more sensing segments and the one or more sensing segments of each optical fiber are linearly spaced apart from the one or more sensing segments of the adjacent optical fibers, whereby there is at least one non-analyte-sensing gap between the adjacent sensing segments.

42. The method as claimed in claim 37, further comprising detecting changes in light propagating through the sensing segments with at least one interferometer.

43. The method as claimed in claim 37 further comprising bundling the sensing segments, the input lead segments, and the output lead segments into a single fiber bundle.

44. The method as claimed in claim 37, wherein the input lead portion and the output lead portions comprise the same physical optical fibers and the method further comprises:
receiving optical energy at a proximal end of at least one of the sensing segments; and disposing a reflective element at a distal end of the at least one sensing segment.

45. The method as claimed in claim 37, wherein the input lead portions and the output lead portions comprise the same physical optical fibers and the method further comprises:
receiving optical energy at a proximal end of at least one of the sensing segments;
coupling a proximal end of a lead portion to a distal end of the at least one sensing segment; and
disposing a reflective element at a distal end of the lead portion.

46. The method as claimed in claim 37, wherein the desired locations comprise defined areas and the method further comprises:
controlling optical energy transmission into the input lead portions;
receiving optical energy from the output lead portions; and
processing the received optical energy to determine detection of at least one analyte within any of the defined areas.

47. A chemical sensing apparatus comprising:
a plurality of optical fibers, each optical fiber comprising: one or more distributed intrinsic chemical analyte responsive fiber optic segments and one or more low loss lead portions,
wherein the analyte responsive segments are disposed at desired locations; means for providing optical energy to the optical fibers; and
means for detecting optical energy propagating within the optical fibers.

48. The apparatus according to claim 47, wherein each optical fiber has one analyte-responsive segment and the analyte-responsive segments are disposed in sequential offset lengthwise relationship to provide a substantially continuous analyte-sensing length over a distance.

49. The apparatus according to claim 47, wherein the one or more analyte-responsive segments of each optical fiber are disposed in a sequential spaced apart lengthwise relationship to detect analytes at different and discrete locations.

50. The apparatus according to claim 47, wherein the optical fibers are disposed lengthwise adjacently in one or more fiber carriers.

51. The apparatus as claimed in claim 47, wherein the means for providing optical energy is disposed at proximal ends of the plurality of optical fibers and the means for detecting optical energy is disposed at distal ends of the plurality of optical fibers.

52. The apparatus as claimed in claim 47, wherein the means for providing optical energy and the means for detecting optical energy are disposed at proximal ends of the plurality of optical fibers and means for reflecting optical energy is disposed at distal ends of the plurality of optical fibers.

53. An apparatus for sensing and locating the presence of an analyte comprising:
a plurality of optical fibers disposed lengthwise adjacently and extending either integrally continuously or through connection over a determined length, wherein each optical fiber has a distributed intrinsic analyte-sensing fiber optic segment responsive to the same analyte and each segment being of a determined length less than the entire determined length of the optical fiber;
the analyte-sensing segments of designated adjacent ones of the optical fibers being ordered in sequential lengthwise relationship to each other;
whereby each optical fiber may sense the presence of the analyte along the determined length of the analyte-sensing segment thereof.

54. The apparatus of claim 53 further wherein the analyte-sensing segments are located relative to each other in any selected combination of serial relationship selected from:
(a) offset; and
(b) spaced apart.

55. The apparatus of claim 53 further comprising:
an optical energy source disposed to transmit light into the plurality of optical fibers;
an optical energy detector coupled to the plurality of optical fibers to receive light from the plurality of fibers discriminating each fiber; and
means to detect a change in the received light from each of the optical fibers caused by an analyte in contact with the analyte-sensing segment of the optical fiber.

56. An apparatus for sensing and locating the presence of an analyte comprising;
a plurality of fiber carriers, each having a plurality of peripheral fiber receptacles extending lengthwise thereof and passive structure extending lengthwise thereof and wherein the fiber carriers are end-to-end adjacent;
a plurality of optical fibers, each optical fiber having a distributed intrinsic chemical fiber optic sensing segment and at least one lead portion extending from one or both terminal ends of the sensing segment;
the sensing portion of each optical fiber disposed in a peripheral receptacle of a spine portion and the lead portions of each optical fiber disposed in a passive structure of an adjacent fiber carrier.

* * * * *